United States Patent
Matheny

(10) Patent No.: US 9,066,993 B2
(45) Date of Patent: Jun. 30, 2015

(54) EXTRACELLULAR MATRIX ENCASEMENT STRUCTURES AND METHODS

(71) Applicant: Robert G Matheny, Norcross, GA (US)

(72) Inventor: Robert G Matheny, Norcross, GA (US)

(73) Assignee: CORMATRIX CARDIOVASCULAR, INC., Roswell, GA (US)

( * ) Notice: Subject to any disclaimer, the term of this patent is extended or adjusted under 35 U.S.C. 154(b) by 102 days.

(21) Appl. No.: 13/573,566

(22) Filed: Sep. 24, 2012

(65) Prior Publication Data

US 2013/0023721 A1  Jan. 24, 2013

Related U.S. Application Data

(63) Continuation-in-part of application No. 13/328,287, filed on Dec. 16, 2011.

(51) Int. Cl.

| | | |
|---|---|---|
| *A61K 35/12* | (2015.01) | |
| *A61F 13/00* | (2006.01) | |
| *A61K 9/16* | (2006.01) | |
| *A61L 33/00* | (2006.01) | |
| *A61N 1/362* | (2006.01) | |
| *A61L 27/36* | (2006.01) | |
| *A61L 27/38* | (2006.01) | |
| *A61L 31/00* | (2006.01) | |
| *A61F 2/02* | (2006.01) | |
| *A61K 35/28* | (2015.01) | |
| *A61K 38/18* | (2006.01) | |
| *A61L 27/54* | (2006.01) | |
| *A61F 2/24* | (2006.01) | |
| *A61K 38/00* | (2006.01) | |
| *A61K 35/22* | (2015.01) | |
| *A61K 35/38* | (2015.01) | |

(52) U.S. Cl.
CPC .............. *A61L 27/3633* (2013.01); *A61F 2/24* (2013.01); *A61K 38/005* (2013.01); *A61K 35/22* (2013.01); *A61K 35/38* (2013.01); *A61K 35/12* (2013.01); *A61L 27/3641* (2013.01); *A61L 27/3839* (2013.01); *A61L 31/005* (2013.01); *A61L 27/3629* (2013.01); *A61L 27/3679* (2013.01); *A61L 27/3804* (2013.01); *A61F 2/02* (2013.01); *A61K 35/28* (2013.01); *A61K 38/18* (2013.01); *A61K 38/1825* (2013.01); *A61L 27/54* (2013.01)

(58) Field of Classification Search
CPC ............. A61F 2/02; A61F 2/24; A61K 35/12; A61K 35/22; A61K 35/38; A61K 38/005; A61L 27/3633; A61L 27/3679
USPC ............. 424/422, 490, 572; 427/2.24; 600/16
See application file for complete search history.

(56) References Cited

U.S. PATENT DOCUMENTS

| | | | |
|---|---|---|---|
| 2009/0204228 A1* | 8/2009 | Hiles | |
| 2010/0262221 A1* | 10/2010 | Schafer et al. | |
| 2012/0100185 A1* | 4/2012 | Wen et al. | |
| 2012/0156255 A1* | 6/2012 | Singh et al. | |

* cited by examiner

*Primary Examiner* — Shin Lin Chen

(74) *Attorney, Agent, or Firm* — Francis Law Group

(57) ABSTRACT

A remodelable encasement structure comprising a pouch formed from at least one sheet of bioremodelable material, the pouch having an internal region configured to receive a device therein, the bioremodelable material comprising an extracellular matrix (ECM) composition that includes an ECM scaffold component derived from a mammalian source and at least a bioactive component selected from the group consisting of a statin and a chitin derivative.

3 Claims, 2 Drawing Sheets

EXTRACELLULAR MATRIX ENCASEMENT STRUCTURES AND METHODS

CROSS-REFERENCES TO RELATED APPLICATIONS

This application is a continuation-in-part of U.S. application Ser. No. 13/328,287, filed on Dec. 16, 2011.

FIELD OF THE INVENTION

The present invention relates to implantable devices. More particularly, the present invention relates to implantable structures and devices; particularly, medical devices encased in extracellular matrix (ECM) based pouches and/or include ECM based coatings that effectuate modulated healing of damaged tissue and regeneration of new tissue structures with site-specific structural and functional properties.

BACKGROUND OF THE INVENTION

As is well known in the art, treatment of various medical conditions commonly involves implantation of medical devices and/or insertion of medical instruments into a body. Illustrative is the implantation or deployment of heart valves to regulate the flow of blood through cardiovascular vessels, and pacemakers to control abnormal heart rhythms.

Implantable medical devices; particularly, cardiovascular implants, have unique blood biocompatibility requirements to ensure that the device is not rejected (as in the case of natural tissue materials for heart valves and grafts for heart transplants) or that adverse thrombogenic (clotting) or hemodynamic (blood flow) responses are avoided.

Several cardiovascular implants, such as heart valves, are formed from natural tissue. Illustrative are the heart valves disclosed in U.S. Pat. Nos. 6,719,788 and 5,480,424 to Cox. The disclosed bioprostheses can, however, be affected by gradual calcification, which can, and in many instances will, lead to the eventual stiffening and tearing of the implant.

Many non-bioprosthetic implants are, however, fabricated from various metals and polymeric materials, and other exotic materials, such as pyrolytic carbon-coated graphite.

For example, pacemakers, defibrillators, leads, and other similar cardiovascular implants are often fabricated from Ni—Co—Cr alloy, Co—Cr—Mo alloy, titanium, and Ti-6Al-4V alloy, stainless steel, and various biocompatible polymeric materials. Artificial heart valves are often fabricated from various combinations of nylon, silicone, titanium, Teflon™, polyacetal, graphite and pyrolytic carbon.

Artificial hearts and ventricular assist devices are often fabricated from various combinations of stainless steel, cobalt alloy, titanium, Ti-6Al-4V alloy, carbon fiber reinforced composites, polyurethanes, Biolon™, Hemothane™, Dacron™, polysulfone, and other thermoplastics.

Finally, catheters and guide wires are often fabricated from Co—Ni or stainless steel wire. In many instances, the wire is encased in a polymeric material.

As is well known in the art, several major problems are often encountered when a medical device (or other device, e.g. tracking apparatus) fabricated from one of the aforementioned materials is implanted in the body. A major problem that is often encountered after implantation of such a device in the body is inflammation of surrounding tissue.

Another major problem is the high incidence of infection.

A further problem that is often encountered after implantation of the medical device in the body is the formation of blood clots (thrombogenesis).

One additional problem that is also often encountered is the degradation, e.g., corrosion, of medical device leads and, thereby, premature failure of the device after implantation in the body.

Most medical devices are designed to be implanted in the body for an extended period of time. However, when a harsh biological response (or premature failure of the device) is encountered after implantation, it is often necessary to remove the device through a secondary surgical procedure, which can, and in many instances will, result in undesirable pain and discomfort to the patient, and possibly additional trauma to the adjacent tissue. In addition to the pain and discomfort, the patient must be subjected to an additional time consuming and complicated surgical procedure with the attendant risks of surgery.

There is thus a need to provide medical devices that are configured for implantation in the body, and substantially reduce or eliminate the harsh biological responses associated with conventional implanted medical devices, including inflammation, infection and thrombogenesis.

It is therefore an object of the present invention to provide encasement structures that are configured to encase a medical device therein and that substantially reduce or eliminate the harsh biological responses associated with conventional implanted medical devices, including inflammation, infection and thrombogenesis, when implanted in the body.

It is another object of the present invention to provide ECM encasement structures that are configured to encase a medical device therein, and effectively improve biological functions and/or promote modulated healing of adjacent tissue and the growth of new tissue when implanted in the body.

It is another object of the present invention to provide ECM encasement structures that are configured to encase a medical device therein and administer one or more pharmacological or therapeutic agents when implanted in the body.

It is yet another object of the present invention to provide medical devices that are configured for insertion or implantation in the body and exhibit enhanced biocompatibility and hemocompatibility when inserted or implanted therein.

SUMMARY OF THE INVENTION

The present invention is directed to extracellular matrix (ECM) structures and compositions for encasing devices; particularly, medical devices.

In some embodiments of the invention, the ECM structures include a pocket or pouch that is configured to receive a device therein. In a preferred embodiment, the device comprises a medical device.

In a preferred embodiment, the pouch comprises (or is constructed of) an ECM composition that includes at least one ECM material.

In other embodiments of the invention, there are provided medical devices that are configured for insertion or implantation in the body and include at least one coating of an ECM composition; the ECM composition similarly including at least one ECM material.

According to the invention, the medical devices and associated components can comprise, without limitation, a pacemaker, defibrillator, synthetic heart valve, ventricular assist device, artificial heart, physiological sensor, catheter, and the electrical leads and lines associated therewith.

According to the invention, the ECM material can be derived from various mammalian tissue sources including, without limitation, the small intestine, large intestine, stomach, lung, liver, kidney, pancreas, placenta, heart, bladder, prostate, tissue surrounding growing enamel, tissue surrounding growing bone, and any fetal tissue from any mammalian organ.

In some embodiments, the ECM compositions further include one or more additional biologically active components to facilitate the treatment of damaged tissue and/or the tissue regenerative process.

In some embodiments, the ECM compositions thus include at least one pharmacological agent or composition, which can comprise, without limitation, antibiotics or antifungal agents, anti-viral agents, anti-pain agents, anesthetics, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or anti-thrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent specifically comprises an anti-inflammatory agent or composition.

In some embodiments of the invention, the biologically active component comprises a statin. According to the invention, suitable statins include, without limitation, atorvastatin, cerivastatin, fluvastatin, lovastatin, mevastatin, pitavastatin, pravastatin, rosuvastatin, and simvastatin.

In some embodiments of the invention, the biologically active component comprises chitosan.

In some embodiments of the invention, the biologically active component comprises a cell.

In some embodiments of the invention, the biologically active component comprises a protein.

According to the invention, upon deployment of an encased medical device of the invention, i.e. an ECM encasement structure having a medical device therein or a medical device (or instrument) coated with an ECM composition of the invention, modulated healing and regeneration of tissue structures with site-specific structural and functional properties are effectuated.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1:
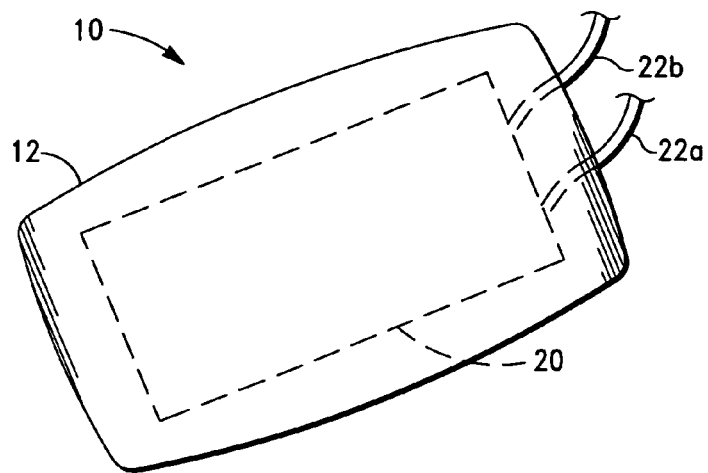
FIG. 1 is a perspective view of one embodiment of an ECM encasement structure, in accordance with the invention.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that, although the present invention is described and illustrated in connection with encased medical devices, the invention is not limited to encased medical devices. According to the invention, the extracellular matrix (ECM) structures and compositions of the invention can also be employed to encase other devices, including, by way of example, a tracking device.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "an active" includes two or more such actives and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The term "medical device", as used herein, means and includes any device configured for insertion or implantation in the body of a warm blooded mammal, including humans and primates; avians; domestic household or farm animals, such as cats, dogs, sheep, goats, cattle, horses and pigs; laboratory animals, such as mice, rats and guinea pigs; fish; reptiles; zoo and wild animals; and the like. The term "medical device" thus includes, without limitation, a pacemaker, defibrillator, synthetic heart valve, ventricular assist device, artificial heart, physiological sensor, catheter, and associated components thereof, including electrical leads and lines associated therewith.

The terms "extracellular matrix" and "ECM material", are used interchangeably herein, and mean and include a collagen-rich substance that is found in between cells in animal tissue and serves as a structural element in tissues. The ECM material typically comprises a complex mixture of polysaccharides and proteins secreted by cells.

According to the invention, the ECM material can be isolated from small intestine submucosa, stomach submucosa, urinary bladder submucosa, tissue mucosa, dura mater, liver basement membrane, pericardium or other tissues. Following isolation and treatment, it is commonly referred to as extracellular matrix or ECM material.

The terms "pharmacological agent", "pharmaceutical agent", "agent", "active agent", "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "pharmaceutical agent", "agent", "active agent", "drug" and "active agent formulation" thus mean and include, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "pharmaceutical agent", "agent", "active agent", "drug" and "active agent formulation" also mean and include chitin, chitosan, and derivations thereof.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues. Anti-inflammatory agents thus include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, morniflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The terms "active agent formulation", "pharmacological agent formulation" and "agent formulation", are also used interchangeably herein, and mean and include an active agent optionally in combination with one or more pharmaceutically acceptable carriers and/or additional inert ingredients. According to the invention, the formulations can be either in solution or in suspension in the carrier.

The term "pharmacological composition", as used herein, means and includes a composition comprising a "pharmacological agent" and/or an "extracellular matrix material" and/or a "pharmacological agent formulation."

The term "therapeutically effective", as used herein, means that the amount of the "pharmacological composition" and/or "pharmacological agent" and/or "active agent formulation" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "prevent" and "preventing" are used interchangeably herein, and mean and include reducing the frequency or severity of a disease or condition. The term does not require an absolute preclusion of the disease or condition. Rather, this term includes decreasing the chance for disease occurrence.

The terms "treat" and "treatment" are used interchangeably herein, and mean and include medical management of a patient with the intent to cure, ameliorate, stabilize, or prevent a disease, pathological condition, or disorder. The terms include "active treatment", i.e. treatment directed specifically toward the improvement of a disease, pathological condition, or disorder, and "causal treatment", i.e. treatment directed toward removal of the cause of the associated disease, pathological condition, or disorder.

The terms "treat" and "treatment" further include "palliative treatment", i.e. treatment designed for the relief of symptoms rather than the curing of the disease, pathological condition, or disorder, "preventative treatment", i.e. treatment directed to minimizing or partially or completely inhibiting the development of the associated disease, pathological condition, or disorder, and "supportive treatment", i.e. treatment employed to supplement another specific therapy directed toward the improvement of the associated disease, pathological condition, or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims, including any amendments made during the pendency of this application, and all equivalents of those claims as issued.

As stated above, it is understood that, although the present invention is described and illustrated in connection with encased medical devices, the invention is not limited to encased medical devices. According to the invention, the extracellular matrix (ECM) structures and compositions of the invention can also be employed to encase other devices, including, by way of example, a tracking device.

As discussed above, in one embodiment, the present invention is directed to extracellular matrix (ECM) structures and compositions for encasing medical devices.

In one embodiment of the invention, the ECM encasement structures include an ECM based pocket or pouch that is configured to receive a medical device therein. In another embodiment of the invention, there is provided a medical device (or instrument) that includes at least one coating of an ECM composition; the ECM composition similarly including at least one ECM material.

According to the invention, upon deployment of an ECM encasement structure having a medical device therein or a medical device (or instrument) coated with an ECM composition of the invention, modulated healing and regeneration of tissue structures with site-specific structural and functional properties are effectuated.

The phrase "modulated healing", as used herein, and variants of this language generally refer to the modulation (e.g., alteration, delay, retardation, reduction, etc.) of a process involving different cascades or sequences of naturally occurring tissue repair in response to localized tissue damage or injury, substantially reducing their inflammatory effect. Modulated healing, as used herein, includes many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other.

For example, in some embodiments, the ECM compositions of the invention are specifically formulated (or designed) to alter, delay, retard, reduce, and/or detain one or more of the phases associated with healing of damaged tissue, including, but not limited to, the inflammatory phase (e.g., platelet or fibrin deposition), and the proliferative phase.

In some embodiments, "modulated healing" refers to the ability of an ECM composition to alter a substantial inflammatory phase (e.g., platelet or fibrin deposition) at the beginning of the tissue healing process. As used herein, the phrase "alter a substantial inflammatory phase" refers to the ability of an ECM composition to substantially reduce the inflammatory response at an injury site.

In such an instance, a minor amount of inflammation may ensue in response to tissue injury, but this level of inflammation response, e.g., platelet and/or fibrin deposition, is substantially reduced when compared to inflammation that takes place in the absence of an ECM composition of the invention.

For example, the ECM compositions discussed herein have been shown experimentally to delay or alter the inflammatory response associated with damaged tissue, as well as excessive formation of connective fibrous tissue following tissue damage or injury. The ECM compositions have also been shown experimentally to delay or reduce fibrin deposition and platelet attachment to a blood contact surface following tissue damage.

In some embodiments of the invention, "modulated healing" refers to the ability of an ECM composition of the invention to induce host tissue proliferation, bioremodeling, including neovascularization, e.g., vasculogenesis, angiogenesis, and intussusception, and regeneration of tissue structures with site-specific structural and functional properties.

Accordingly, the ECM compositions discussed herein provide an excellent bioabsorbable cellular interface suitable for use with a medical device or surgical instrument.

As indicated above, in one embodiment of the invention, the ECM encasement structures include an ECM based pocket or pouch that is configured to receive a medical device therein. According to the invention, the encased medical device and associated components can comprise, without limitation, a pacemaker, defibrillator, synthetic heart valve, ventricular assist device, artificial heart, physiological sensor, catheter, and the electrical leads and lines associated therewith.

According to the invention, the entire medical device or a portion thereof can be encased in the ECM based pouch. Thus, in some embodiments of the invention, the device housing and a portion of the device leads are encased in an ECM based pouch. In the noted embodiments, the device leads can also be coated with an ECM composition of the invention.

In a preferred embodiment, the ECM pouch comprises (or is constructed of) an ECM composition that includes at least one ECM material (hereinafter "ECM pouch"). According to the invention, the ECM pouch can comprise various shapes and sizes to accommodate virtually all shapes and sizes of medical devices.

As also indicated above, in other embodiments of the invention, there are provided medical devices that include at least one coating of an ECM composition; the ECM composition similarly including at least one ECM material. According to the invention, the medical devices can similarly include, without limitation, the aforementioned devices and associated components, as well as surgical instruments.

According to the invention, the ECM material can be derived from various mammalian tissue sources and methods for preparing same, such as disclosed in U.S. Pat. Nos. 7,550, 004, 7,244,444, 6,379,710, 6,358,284, 6,206,931, 5,733,337 and 4,902,508 and U.S. application Ser. No. 12/707,427; which are incorporated by reference herein in their entirety.

The mammalian tissue sources include, without limitation, the small intestine, large intestine, stomach, lung, liver, kidney, pancreas, placenta, heart, bladder, prostate, tissue surrounding growing enamel, tissue surrounding growing bone, and any fetal tissue from any mammalian organ.

As is also well known in the art, the urinary bladder submucosa is an extracellular matrix that has the tunica mucosa (which includes the transitional epithelial layer and the tunica propria), a submucosal layer, 3 layers of muscularis, and the adventitia (a loose connective tissue layer). This general configuration is true also for small intestine submucosa (SIS) and stomach submucosa (SS).

Other tissues, such as the liver and pancreas have extracellular matrix called basement membrane. Basement membrane generally does not demonstrate the kind of tensile strength found in submucosa. However, other useful properties may be opportunistically employed from the extracellular matrices of such tissues as the liver, pancreas, placenta and lung tissues; all of which have either basement membrane for extracellular matrix or interstitial membrane (as with the lung). For example, the pancreatic extracellular membrane supports beta islet cells that are critical to pancreatic function. Also, for example, the liver is one tissue known to be able to regenerate itself and therefore special qualities may be present in the liver basement membrane that help facilitate that process.

The extracellular matrices surrounding developing tooth enamel and developing bone also have particular advantages over other matrices in that they support the growth and differentiation of the hard tissues of bone and enamel.

According to the invention, matrices can be used in whole or in part, so that, for example, an extracellular matrix can contain just the basement membrane (or transitional epithelial layer) with the subadjacent tunica propria, the tunica submucosa, tunica muscularis, and tunica serosa. The extracellular matrix component of the composition can contain any or all of these layers, and thus could conceivably contain only the basement membrane portion, excluding the submucosa. However, generally, and especially since the submucosa is thought to contain and support the active growth factors, cytokines and other proteins necessary for in vivo tissue regeneration, the matrix composition from any given source will contain the active extracellular matrix portions that support cell development and differentiation and tissue regeneration.

For purposes of this invention, the extracellular matrix from any of the mammalian tissue consists of several basically inseparable layers broadly termed extracellular matrix. For example, where it is thought that separating a basement membrane from the submucosa is considered to be very difficult, if not impossible, because the layers are thin and it is not possible to delaminate them from each other, the extracellular matrix from that particular layer will probably necessarily contain some basement membrane with the submucosa.

As stated above, in some embodiments of the invention, the ECM structure (or material thereof) includes at least one bioactive component. In some embodiments, the bioactive component comprises a pharmacological agent or composition, i.e. an agent that is capable of producing a desired biological effect in vivo, such as stimulation or suppression of cell division, stimulation or suppression of apoptosis, stimulation or suppression of an immune response, anti-bacterial activity, etc.

Suitable pharmacological agents (and/or compositions) include, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

According to the invention, the amount of a pharmacological agent added to an ECM composition of the invention will, of course, vary from agent to agent. For example, in one embodiment, wherein the pharmacological agent comprises dicloflenac (Voltaren®), the amount of dicloflenac included in the ECM composition is preferably in the range of 10 µg-75 mg.

In some embodiments of the invention, the pharmacological agent specifically comprises an anti-inflammatory agent. According to the invention, suitable anti-inflammatory agents include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, morniflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

According to the invention, the amount of an anti-inflammatory added to an ECM composition of the invention can similarly vary from anti-inflammatory to anti-inflammatory. For example, in one embodiment of the invention, wherein the pharmacological agent comprises ibuprofen (Advil®), the amount of ibuprofen included in the ECM composition is preferably in the range of 100 µg-200 mg.

In some embodiments of the invention, the pharmacological agent comprises a statin, i.e. a HMG-CoA reductase inhibitor. According to the invention, suitable statins include, without limitation, atorvastatin (LIPITOR®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

Applicant has found that statins exhibit numerous beneficial properties that provide several beneficial biochemical actions or activities. The properties and beneficial actions resulting therefrom are discussed in detail below.

Anticholesterolemic Properties/Actions

As is well known in the art, statins are a class of drugs that primarily function to lower levels of cholesterol production in the liver. Lower levels of cholesterol are achieved by virtue of the statins limiting the production of mevalonate in the cholestrol biosynthetic pathway. Statins competitively inhibit HMG-CoA reductase, which, because the molecules are so similar, results in the statins actually taking the place of the HMG-CoA reductase in the cholesterol biosynthetic pathway and reducing the rate at which the mevalonate is produced; subsequently lowering the rate at which cholesterol is produced in the liver.

Anti-Inflammatory Properties/Actions

Statins also have numerous additional favorable effects on cellular structures and processes. One specific example is that statins can, and in many instances will, aid in the reduction of thromboxane A2 ($TXA_2$), which then lowers platelet activation.

$TXA_2$ is also known as a vasoconstrictor and is especially important during tissue injury and inflammation due to its impact on platelet activation and aggregation, as well as its ability to augment the expression of adhesion molecules and chemokines. This allows statins to aid in the reduction of inflammation by the reduction of $TXA_2$, which results in less vascoconstriction, less platelet activation and aggregation, as well as reduced augmentation of adhesion molecules and chemokines.

Statins further impact cellular structures and processes by blocking ras homilog gene family, member A (RhoA) activation. Blocking RhoA activation impacts numerous systems, such as macrophage growth, tissue plasminogen activators (t-PA), plasminogen activator inhibitor type 1 (PAI-1), smooth muscle cell (SMC) proliferation, nitric oxide (NO) production, endothelins, and angiotensin receptors. As discussed below, when statins block RhoA activation, the resultant impact can be seen in many physiological structures and processes, including inflammation, smooth muscle cell production and size, and vasoconstriction.

Blocking RhoA activation reduces macrophage growth and, thereby, matrix metalloprotinases (MMPs), i.e. a family of zinc-dependent proteases that play a role in cellular behavior (i.e. proliferation, migration, apoptosis, differentiation, ECM modulation, immune response, etc., and tissue factors (TF). A reduction in MMPs and TF limit the reduction of ECM proteins.

MMPs are produced by activated neutrophils and macrophages (inflammatory cells) and play on important part in wound healing and inflammation.

Statins facilitate the reduction of inflammatory factors by inhibiting the Fc-receptor present on Type I (M1) macropages, which results in reduced production of MMPs. Lowered MMPs also results in a lowered presence of thrombi, as the MMPs attach to ECM present in thrombi or damaged ECM at wound sites.

Macrophage growth reduction also results in lowered presence of tissue factor (TF); a protein necessary for the initiation of thrombin formation. A lowered presence of TF results in a lowered presence of thrombi; particularly, in the cardiovascular system, especially in conjunction with reduced MMPs.

Plaque Stabilizing Properties/Actions

Reduced MMPs and reduced TF also results in increased plaque stability, which can help to prevent stroke or myocardial infarction by reducing the probability of plaque breaking off and becoming lodged within a smaller vessel. Plaque stability further aids in reduction of atherosclerosis.

Fibrinolysis Properties/Actions

Blocking RhoA activation also affects the presence of tissue plasminogen activators (t-PA) and plasminogen activator inhibitor Type 1 (PAI-1). T-PA is a protein involved in the breakdown of blood clots. As an enzyme, it catalyzes the conversion of plasminogen to plasmin; the major enzyme responsible for clot breakdown (fibrinolysis).

PAI-1 is a protein that functions as the principal inhibitor oft-PA and, hence, is the principal inhibitor of fibrinolysis. With t-PA presence raised and PAI-1 diminished by blocking RhoA activation caused by statins, a reduced thrombotic effect is realized due to the reduced opportunity for fibrin to form the polymeric mesh of a hemostatic plug. The reduced MMPs and TF that result from the presence of a statin work in concert with the increased t-PA and reduced PAI-1 to further reduce the potential for thrombii.

NO Regulation Properties/Actions

Blocking RhoA activation also affects the presence of Nitric Oxide (NO). As is well known in the art, the endothelium uses NO to signal the surrounding smooth muscles to relax, resulting in vasodialation and increased blood flow. NO contributes to vessel homeostasis by, among other things, inhibiting vascular smooth muscle function, platelet aggregation, and leukocyte adhesion to the endothelium. These factors are what allow NO to aid in the reduction of endothelial dysfunction when modulated with a statin. The reduction of leukocyte adhesion is a specific example of how the NO production associated with a statin aids in the reduction of inflammation.

RhoA Activation Blocking Properties/Actions

The administration of statins can also affect the presence of endothelins and agiotensin receptors. Endothelins are proteins that constrict blood vessels and raise blood pressure. There are three isoforms of endothelins; ET-1, ET-2, and ET-3, with ET-1 being the isoform primarily affected by statins and RhoA activation blocking. Secretion of ET-1 from the endothelium signals vasoconstriction and influences local cellular growth and survival. ET-1 has been implicated in the development and progression of vascular disorders, such as atherosclerosis and hypertension. The decrease in the presence of ET-1 associated with statins and RhoA activation blocking results in decreased vasoconstriction and progression of the aforementioned disorders.

Angiotensin receptors are protein coupled receptors that are responsible for the signal transduction of the vasoconstricting stimulus of the main effector hormone angiotensin II. Angiotensin Receptor II Type I (AT-1) is the angiotensin receptor primarily affected by statin administration and RhoA activation blocking. AT-1 mediates, among other things, vasocontraction, cardiac hypertrophy, and vascular smooth muscle cell proliferation. The reduction in AT-1 that accompanies statin administration and RhoA activation blocking results in reduced vasoconstriction.

C-Reactive Protein Reduction Properties/Actions

C-Reactive Proteins (CRP) are also influenced by statin administration. CRP are found in the blood; the levels of which deviate in response to varying levels of inflammation. CRP levels diminish in response to statin administration and, thereby, the reduction in inflammation.

Adhesion Molecule Reduction Properties/Actions

Adhesion molecules are proteins that are located on the cell surface and impact inflammation and thrombin formation in endothelial cells. With a higher incidence of inflammation comes a higher incidence of cell adhesion molecules. Statins reduce the presence of adhesion molecules on the endothelium. This helps to reduce inflammation by removing the attachment mechanism for leukocytes and subsequent plaque buildup, the result being a lowered probability of atherosclerosis.

Rac-1 Reduction Properties/Actions

Rac-1 is also a protein found in human cells. Rac-1 plays a central role in endothelial cell migration, tubulogenesis, adhesion, and permeability. The expression of Rac-1 can, and in many instances will, be reduced by the administration of a statin. The decrease in the presence of Rac-1 also results in the decrease of reactive oxygen species (ROS). i.e. chemically reactive molecules that have important roles in cell signaling and homeostasis.

Systemic administration of a statin typically ranges from 10 mg-80 mg daily. However, it is well known in the art that, in some instances, the dosage of a statin that is required to reach a therapeutically effective local level can result in various toxicities within different organ systems, such as the liver and musculature. However, due to the direct nature of the administration of statins when incorporated in or provided in contact with an ECM material or composition of the invention, therapeutically effective dosages can be much smaller, thereby, substantially reducing the possibility of systemic toxicities.

According to the invention, the amount of a statin added to a pharmacological composition of the invention is preferably less than 20 mg, more preferably, less than approximately 10 mg.

In some embodiments of the invention, the ECM material includes 100 ug-5 mg of a statin. In some embodiments of the invention, the ECM material includes 500 ug-2 mg of a statin.

In some embodiments of the invention, the bioactive component comprises chitosan or a derivative thereof.

Chitosan exhibits a wide range of favorable biochemical properties that make it an outstanding agent for use in the medical field. The biochemical properties of chitosan, which are discussed below, include biocompatibility, biodegradability and non-toxicity. Additional properties, such as analgesic, hemostatic, antimicrobial, and antioxidant have also been reported. See Aranaz, et al., *Functional Characterization of Chitin and Chitosan*, Current Chemical Biology, vol. 3, pp. 203-230 (2009); and Kumar MNVR, *A Review of Chitin and Chitosan Applications*, React. Funct. Polm., vol. 46, pp. 1-27 (2000).

As is well known in the art, chitin and chitosan are typically described as a family of linear polysaccharides consisting of varying amounts β (1-4) linked residues of N-acetyl-2 amino-2-deoxy-D-glucose and 2-amino-2-deoxy-Dglucose residues ("D" units or residues).

Chitin samples have a low amount of D units and hence the polymer is insoluble in acidic aqueous media. On the other hand, the amount of D units in chitosan samples is high enough to allow the polymer to dissolve in acidic aqueous media. Some authors consider chitosan to be the polymer with at least 60% of D units. See S. Aiba, *Studies on Chitosan: 4. Lysozymic Hydrolysis of Partially N-Acetylated Chitosans*, J. Biol. Macromol., vol. 14(4), pp. 225-228 (1992).

Chitin is the second most abundant natural polymer in nature after cellulose and it is found in the structure of a wide number of invertebrates (crustaceans' exoskeleton, insects' cuticles) and the cell walls of fungi, among others. On the other hand, chitosan only occurs naturally in some fungi (Mucoraceae).

Chitosan is prepared by hydrolysis of acetamide groups of chitin. This is normally conducted by severe alkaline hydrolysis treatment due to the resistance of such groups imposed by the trans arrangement of the $C_2$-$C_3$ substituents in the sugar ring.

As stated and discussed in detail below, chitosan exhibits a wide range of favorable biochemical properties that make it an outstanding agent for use in the medical field.

Biodegradability Properties/Actions

Although chitosan is absent from mammals, chitosan can be readily degraded in vivo by several proteases (lysozyme, papain, pepsin, etc.). It has also been found that the biodegradation of chitosan leads to the release of non-toxic oligosaccharides of variable length, which can be subsequently incorporated to glycosaminoglycans and glycoproteins, to metabolic pathways or be excreted. See Pangburn, et al., *Lysozyme Degradation of Partially Deacetylated Chitin, its Films and Hydrogels*, vol. 3(2), pp. 105-108 (1982).

Biocompatibility Properties/Actions

Chitosan also exhibits very good compatibility; particularly, cytocompatibility.

The enhanced cytocompatibility of chitosan has been proven in vitro with myocardial, endothelial and epithelial cells, fibroblast, hepatocytes, condrocytes and keratinocytes. See Chatelet, et al., *Influence of the Degree of Acetylation on Some Biological Properties of Chitosan Films*, Biomaterials, vol. 22(3), pp. 261-268 (2001).

Analgesic Properties/Actions

It has been reported that chitosan exhibits very favorable analgesic properties (or effects). Okamoto, et al. specifically studied the analgesic effect of chitosan on inflammatory pain due to intraperitoneal administration of acetic acid. See Okamoto, et al., *Analgesic Effects of Chitin and Chitosan*, Carbohyd. Poly., vol. 49, pp. 249-252 (2002).

Okamoto, et al. found that, due to its polycationic nature, the free primary amino groups of chitosan can protonate in the presence of proton ions and, thereby, reduce the pH, which is a primary cause of the analgesic properties. From experimental data, it was also concluded that the analgesic effect was due primarily to the absorption of bradykinin, one of the main components (or substances) related to pain.

Haemostatic Properties/Actions

It has also been reported that chitosan, as well as sulphated chitosan oligomers, exhibit anticoagulant activity tested in vitro. The anticoagulant activity of chitosan is deemed to be related to its positive charge, since red blood cells' membranes are negatively charged. See Rao, et al., *Use of Chitosan as Biomaterial: Studies on its Safety and Hemostatic Potential*, J. Biomed. Mat. Res., vol. 34, pp. 21-28 (1997).

Permeation Enhancing Properties/Actions

It has also been reported that chitosan acts as a permeation enhancer by opening epithelial tight junctions. The mechanism underlying this behavior is deemed to be based on the interaction of positively charged chitosan and the cell membrane resulting in a reorganization of the tight junction-associated proteins. See Smith, et al., *Effect of Chitosan on Epithelial Cell Tight Junctions*, Pharm. Res., vol. 21(1), pp. 43-49 (2004).

Antimicrobial Properties/Actions

The antimicrobial activity of chitin, chitosan, and their derivatives against different groups of microorganisms, such as bacteria, yeast, and fungi, has also received considerable attention in recent years. Two main mechanisms have been suggested as the cause of the inhibition of microbial cells by chitosan.

The first mechanism comprises the interaction with anionic groups on the cell surface, due to chitosan's polycationic nature, causes the formation of an impermeable layer around the cell, which prevents the transport of essential solutes.

The second mechanism involves the inhibition of the RNA and protein synthesis by permeation into the cell nucleus. See Liu et al., *Antibacterial Action of Chitosan and Carboxymathylated Chitosan*, J. Appl. Polym. Sci., vol. 79(7), pp. 1324-1335 (2001).

Antioxidative Properties/Actions

Chitosan has also shown a significant scavenging capacity against different radical species; the results being comparable to those obtained with commercial antioxidants. See Park, et al., *Free Radical Scavenging Activities of Differently Deacetylated Chitosans*, Carbohyd. Polym., vol. 55(1), pp. 17-22 (2004).

Tissue Repair Properties/Actions

By virtue of the above discussed properties of chitosan, chitosan can and in most instances will, enhance the repair of damaged tissue. Indeed, it has been found that chitosan activates immunocytes and inflammatory cells, such as PMN, macrophage, fibroblasts and angioendothelial cells. See Ueno, et al., *Topical Formulations and Wound Healing Applications of Chitosan*, Adv. Drug Del. Res., vol. 52, pp. 105-115 (2001).

Chitosan oligomers have also exhibited tissue repair properties. It has been suggested that the tissue repair properties are due to their ability to stimulate fibroblast production by affecting the fibroblast growth factor. Subsequent collagen production further facilitates the formation of connective tissue.

According to the invention, the amount of chitosan added to a pharmacological composition of the invention is preferably less than 50 ml, more preferably, less than approximately 20 ml.

In some embodiments of the invention, the chitosan is incorporated in a polymeric network, such as disclosed in U.S. Pub. Nos. 2008/0254104 and 2009/0062849, which are incorporated herein in their entirety.

In some embodiments of the invention, the bioactive component comprises a cell. According to the invention, the cell can comprise, without limitation, a stem cell, such as, for example, a human embryonic stem cell, fetal cell, fetal cardiomyocyte, myofibroblast, mesenchymal stem cell, autotransplanted expanded cardiomyocyte, adipocyte, totipotent cell, pluripotent cell, blood stem cell, myoblast, adult stem cell, bone marrow cell, mesenchymal cell, embryonic stem cell, parenchymal cell, epithelial cell, endothelial cell, mesothelial cell, fibroblast, myofibroblast, osteoblast, chondrocyte, exogenous cell, endogenous cell, stem cell, hematopoetic stem cell, pluripotent stem cell, bone marrow-derived progenitor cell, progenitor cell, myocardial cell, skeletal cell, undifferentiated cell, multi-potent progenitor cell, unipotent progenitor cell, monocyte, cardiomyocyte, cardiac myoblast, skeletal myoblast, macrophage, capillary endothelial cell, xenogenic cell, and allogenic cell.

In some embodiments of the invention, the bioactive component comprises a protein. According to the invention, the protein can comprise, without limitation, a growth factor, collagen, proteoglycan, glycosaminoglycan (GAG) chain, glycoprotein, cytokine, cell-surface associated protein, cell adhesion molecule (CAM), angiogenic growth factor, endothelial ligand, matrikine, matrix metalloprotease, cadherin, immunoglobin, fibril collagen, non-fibrillar collagen, basement membrane collagen, multiplexin, small-leucine rich proteoglycan, decorin, biglycan, fibromodulin, keratocan, lumican, epiphycan, heparan sulfate proteoglycan, perlecan, agrin, testican, syndecan, glypican, serglycin, selectin, lectican, aggrecan, versican, nuerocan, brevican, cytoplasmic domain-44 (CD44), macrophage stimulating factor, amyloid precursor protein, heparin, chondroitin sulfate B (dermatan sulfate), chondroitin sulfate A, heparan sulfate, hyaluronic acid, fibronectin (Fn), tenascin, elastin, fibrillin, laminin, nidogen/entactin, fibulin I, fibulin II, integrin, a transmembrane molecule, platelet derived growth factor (PDGF), epidermal growth factor (EGF), transforming growth factor alpha (TGF-alpha), transforming growth factor beta (TGF-beta), fibroblast growth factor-2 (FGF-2) (also called basic fibroblast growth factor (bFGF)), thrombospondin, osteopontin, angiotensin converting enzyme (ACE), and vascular epithelial growth factor (VEGF).

According to the invention, the bioactive components referenced above can comprise any form. In some embodiments of the invention, the bioactive component or components, e.g. simvastatin and/or chitosan, comprise microcapsules that provide delayed delivery of the agent contained therein.

Additional suitable pharmacological compositions that can be delivered within the scope of the invention are disclosed in Pat. Pub. Nos. 20070014874, 20070014873, 20070014872, 20070014871, 20070014870, 20070014869, and 20070014868; which are expressly incorporated by reference herein in its entirety.

As indicated above, upon deployment of an ECM encasement structure or a medical device (or instrument) coated with an ECM composition of the invention, modulated healing and regeneration of tissue structures with site-specific structural and functional properties is effectuated.

Referring now to FIG. 1, there is shown one embodiment of an ECM encasement structure 10. Enclosed within the ECM structure 10 is a medical instrument 20 and at least a portion of the leads 22a, 22b, associated therewith.

As illustrated in FIG. 1, the ECM encasement structure 10 generally comprises a pocket or pouch 12 having a cavity therein 13. The cavity 13 is sized and configured to receive and contain a medical device 20 therein.

In a preferred embodiment of the invention, the pouch 12 comprises at least one layer or sheet of encasement material constructed of an ECM composition of the invention. According to the invention, the pouch 12 can also include more than one layer of encasement material, e.g. two (2), three (3) encasement layers, etc. The encasement layers can also comprise the same material, i.e. ECM composition, or different materials or compositions.

As indicated above, in some embodiments of the invention, the ECM compositions of the invention include one or more pharmacological agents or compositions, including, for example, an anti-inflammatory. An encasement layer formed from one of the noted ECM compositions will thus also include any pharmacological agents or compositions added to the ECM compositions.

According to the invention, one or more pharmacological agents and/or compositions, such as a statin, can also be deposited on the outer surface of an outer encasement layer.

Figure 2:
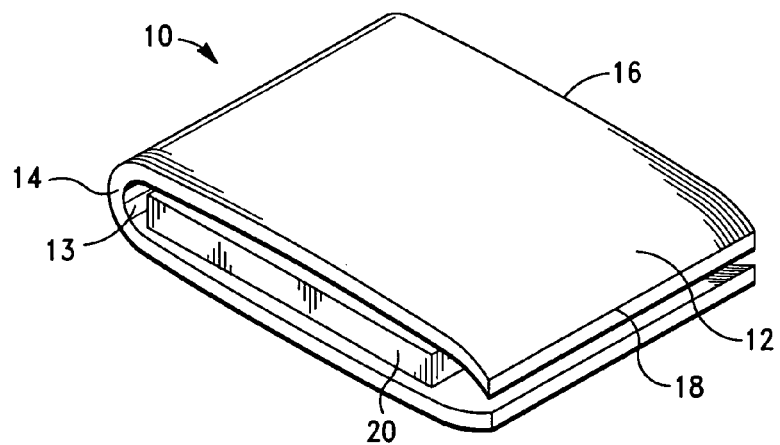
FIG. 2 is a perspective, partial sectional view of an ECM encasement structure, illustrating a folded pre-lamination configuration of an ECM pouch layer, in accordance with the invention.
Figure 3:
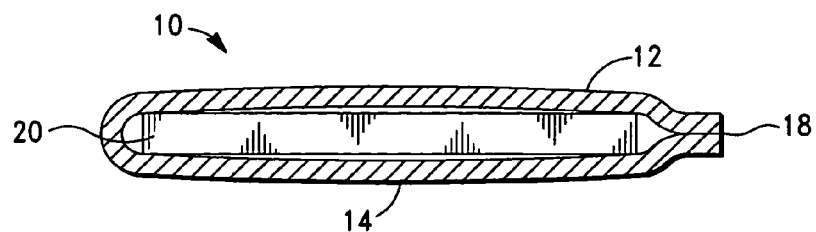
FIG. 3 is a front, partial sectional plan view of the ECM structure shown in FIG. 2, illustrating a laminated ECM pouch layer end, in accordance with the invention.

Referring now to FIG. 2, there is shown a perspective, partial sectional view of the ECM encasement structure 10, showing a folded pre-lamination configuration of the encasement layer (denoted "14"). As illustrated in FIG. 2, in the noted embodiment, the encasement layer 14 comprises a single sheet of encasement material. To form the pouch 12, the encasement layer 14 is folded over and laminated on the end 18 (see FIG. 3) and sides 16.

Figure 4:
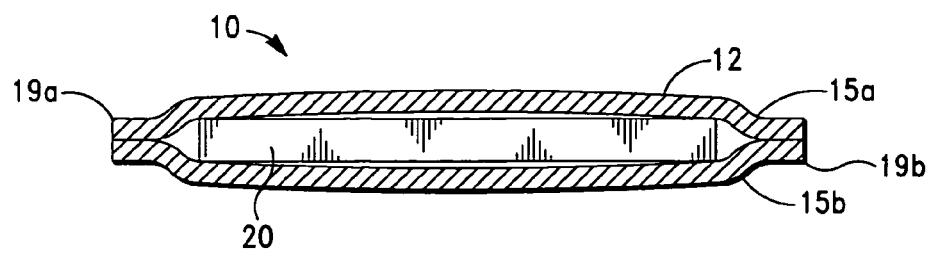
FIG. 4 is a front, partial sectional plan view of another embodiment of an ECM structure, in accordance with the invention.

Referring now to FIG. 4, in some embodiments of the invention, the pouch 12 similarly comprises one encasement layer 14. However, in the noted embodiments, two (2) sheets of encasement material or layers 15a, 15b are employed to form the pouch 12. The layers 15a, 15b are laminated on both ends 19a, 19b, as shown in FIG. 4, and sides.

According to the invention, the sides and ends of encasement layers of the invention can be laminated by various conventional means, such as stitching, including ECM stitches, stapled, adhesives. The encasement layers can also be laminated via microneedles and/or microneedle structures, such as disclosed in U.S. Pat. No. 8,778,012.

As indicated above, in other embodiments of the invention, there are provided medical devices that include at least one coating of an ECM composition of the invention. According to the invention, the medical devices can similarly include, without limitation, the aforementioned devices and associated components, as well as surgical instruments.

Figure 5:
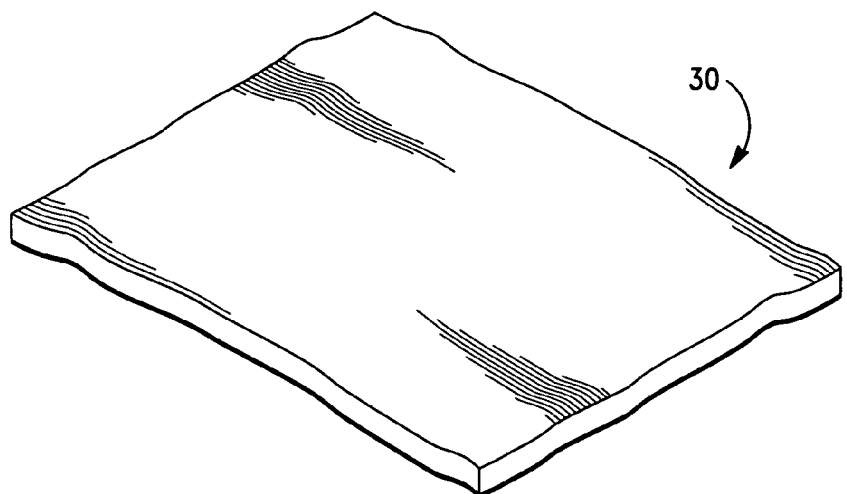
FIG. 5 is a perspective view of one embodiment of a medical device having an ECM composition coating thereon, in accordance with the invention.
Figure 6:
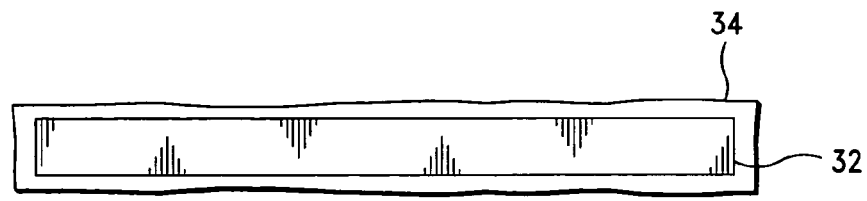
FIG. 6 is a front, partial sectional plan view of the coated medical device shown in FIG. 5, in accordance with the invention.

Referring now to FIGS. 5 and 6, there is shown a medical device (preferably, an implantable medical device) 32 having an ECM composition coating 34 disposed thereon. According to the invention, various conventional means can be employed to form the coated biocompatible and hemocompatable medical device 30, including spray coating, dipping, etc.

As indicated above, upon deployment of an encased medical device of the invention, i.e. an ECM encasement structure or the coated medical device of the invention, modulated healing and regeneration of tissue structures with site-specific structural and functional properties are effectuated.

As will readily be appreciated by one having ordinary skill in the art, the present invention provides numerous advantages compared to prior art vascular endografts. Among the advantages are the following:

The provision of encasement structures that are configured to encase a medical device therein and that substantially reduce or eliminate the harsh biological responses associated with conventional implanted medical devices, including inflammation, infection and thrombogenesis, when implanted in the body.

The provision of ECM encasement structures that are configured to encase a medical device therein, and effectively improve biological functions and/or promote modulated healing of adjacent tissue and the growth of new tissue when implanted in the body.

The provision of ECM encasement structures that are configured to encase a medical device therein and administer one or more pharmacological or therapeutic agents to a subject when implanted in his/her body.

The provision of medical devices that are configured for insertion or implantation in the body and exhibit enhanced biocompatibility and hemocompatibility when inserted or implanted therein.

Without departing from the spirit and scope of this invention, one of ordinary skill can make various changes and modifications to the invention to adapt it to various usages and conditions. As such, these changes and modifications are properly, equitably, and intended to be, within the full range of equivalence of any subsequently proffered claims.

What is claimed is:

1. An implantable medical device, comprising:
a pacemaker comprising an outer surface having at least one coating comprising an extracellular matrix (ECM) composition disposed thereon, said ECM composition coating forming an ECM encasement structure,
said ECM composition comprising acellular ECM from a mammalian tissue source, said tissue source being selected from the group consisting of small intestine submucosa (SIS), urinary bladder submucosa (UBS) and stomach submucosa (SS), said ECM composition further comprising a statin,
said coated pacemaker, when implanted in host tissue of a subject's body, being configured to modulate heart rate of said subject and induce modulated healing, said modulated healing comprising modulation of inflammation of said host tissue, induced tissue proliferation and bioremodeling of said host tissue.

2. The encased medical device of claim 1, wherein said statin is selected from the group consisting of atorvastatin, cerivastatin, fluvastatin, lovastatin, mevastatin, pitavastatin, pravastatin, rosuvastatin and simvastatin.

3. The medical device of claim 1, wherein said pacemaker comprises a plurality of said ECM composition coatings, said plurality of ECM coatings forming a plurality of ECM layers.

* * * * *